(12) United States Patent
Robinson et al.

(10) Patent No.: US 8,571,802 B2
(45) Date of Patent: Oct. 29, 2013

(54) METHOD FOR DETERMINING OPTIMUM INTRAOCULAR LOCATIONS FOR DRUG DELIVERY SYSTEMS

(75) Inventors: Michael R. Robinson, Irvine, CA (US); Joan-En Chang-Lin, Tustin, CA (US); Devin F. Welty, Foothill Ranch, CA (US); Scott M. Whitcup, Laguna Hills, CA (US); Patrick M. Hughes, Aliso Viejo, CA (US)

(73) Assignee: Allergan, Inc., Irvine, CA (US)

( * ) Notice: Subject to any disclaimer, the term of this patent is extended or adjusted under 35 U.S.C. 154(b) by 990 days.

(21) Appl. No.: 11/948,411

(22) Filed: Nov. 30, 2007

(65) Prior Publication Data
US 2008/0181929 A1 Jul. 31, 2008

Related U.S. Application Data

(60) Provisional application No. 60/868,291, filed on Dec. 1, 2006.

(51) Int. Cl.
*G01N 33/50* (2006.01)
(52) U.S. Cl.
USPC .......................................................... 702/19
(58) Field of Classification Search
None
See application file for complete search history.

(56) References Cited

U.S. PATENT DOCUMENTS

| | | | |
|---|---|---|---|
| 4,327,725 A | 5/1982 | Cortese et al. | |
| 4,474,451 A | 10/1984 | Mizokami | |
| 4,521,210 A | 6/1985 | Wong | |
| 4,853,224 A | 8/1989 | Wong | |
| 4,997,652 A | 3/1991 | Wong | |
| 5,164,188 A | 11/1992 | Wong | |
| 5,443,505 A | 8/1995 | Wong et al. | |
| 5,501,856 A | 3/1996 | Ohtori et al. | |
| 5,766,242 A | 6/1998 | Wong et al. | |
| 5,824,072 A | 10/1998 | Wong | |
| 5,869,079 A | 2/1999 | Wong et al. | |
| 6,074,661 A | 6/2000 | Olejnik et al. | |
| 6,331,313 B1 | 12/2001 | Wong et al. | |
| 6,369,116 B1 | 4/2002 | Wong et al. | |
| 6,699,493 B2 | 3/2004 | Wong | |
| 6,713,081 B2 | 3/2004 | Robinson et al. | |
| 6,726,918 B1 | 4/2004 | Wong et al. | |
| 6,899,717 B2 | 5/2005 | Weber et al. | |
| 7,090,681 B2 | 8/2006 | Weber et al. | |
| 2004/0054374 A1 | 3/2004 | Weber et al. | |
| 2005/0154399 A1 | 7/2005 | Weber et al. | |
| 2005/0203542 A1* | 9/2005 | Weber et al. | 606/107 |
| 2006/0182783 A1 | 8/2006 | Hughes et al. | |

OTHER PUBLICATIONS

Kim et al., Preclinical Evaluation of a Novel Episcleral Cyclosporine Implant for Ocular Graft-Versus-Host Disease, Investigative Opthalmology and Visual Science, Feb. 2005, vol. 46, No. 2, pp. 655-662.*
Ashton et al., Journal of Ocular Pharmacology and Therapeutics, "Review: Implants," 1994, vol. 10, No. 4, pp. 691-701.*
U.S. Appl. No. 10/340,237, filed Jan. 9, 2003, Nivaggioli.
U.S. Appl. No. 10/836,880, filed Apr. 30, 2004, Huang.
U.S. Appl. No. 10/836,911, filed Apr. 30, 2004, Huang.
U.S. Appl. No. 10/837,142, filed Apr. 30, 2004, Hughes.
U.S. Appl. No. 10/837,143, filed Apr. 30, 2004, Huang.
U.S. Appl. No. 10/837,260, filed Apr. 30, 2004, Hughes.
U.S. Appl. No. 10/837,355, filed Apr. 30, 2004, Nivaggioli.
U.S. Appl. No. 10/837,356, filed Apr. 30, 2004, Huang.
U.S. Appl. No. 10/837,357, filed Apr. 30, 2004, Whitcup.
U.S. Appl. No. 10/837,379, filed Apr. 30, 2004, Shiah.
U.S. Appl. No. 10/918,597, filed Aug. 13, 2004, Shiah.
U.S. Appl. No. 10/966,764, filed Oct. 14, 2004, Lyons.
U.S. Appl. No. 1/070,158, filed Mar. 1, 2005, Nivaggioli.
U.S. Appl. No. 11/116,698, filed Apr. 27, 2005, Hughes.
U.S. Appl. No. 11/117,879, filed Apr. 29, 2005, Hughes.
U.S. Appl. No. 11/118,288, filed Apr. 29, 2005, Huang.
U.S. Appl. No. 11/18,519, filed Apr. 29, 2005, Burke.
Antcliff R., et al Marshall J., The pathogenesis of edema in diabetic maculopathy, Semin Ophthalmol 1999; 14: 223-232.
Heller, Biodegradable Polymers in Controlled Drug Delivery, In: CRC Critical reviews in Therapeutic Drug Carrier Systems, vol. 1, CRC Press, Boca Raton, FL 1987, pp. 39-90.
Jaffe et al. Fluocinolone Acetonide Implant (Retisert) for Noninfectious Posterior Uveitis: Thirty-Four-Week Results of a Multicenter Randomized Clinical Study, Ophthalmology, 2006; 113:1020-1027.
Kim et al, controlled Drug release from an ocular implant: an evaluation using dynamic three-dimensional magnetic resonance imaging, Investigative ophthalmology & Visual Science, Aug. 2004, vol. 45, No. 8, pp. 2722-2731.
Robinson et al. A rabbit model for assessing the ocular barriers to the transsleral delivery of triamcinolone acetonide. Exp Eye Res 2006;82:479-487.
USP 23; NF 18 (1995) pp. 1790-1798.
U.S. Appl. No. 11/119,001, filed Apr. 29, 2005, Edelman.
U.S. Appl. No. 11/119,021, filed Apr. 29, 2005, Burke.
U.S. Appl. No. 11/119,024, filed Apr. 29, 2005, Hughes.
U.S. Appl. No. 11/119,463, filed Apr. 29, 2005, Hughes.
U.S. Appl. No. 11/292,544, filed Dec. 2, 2005, Whitcup.

* cited by examiner

*Primary Examiner* — Jason Sims
(74) *Attorney, Agent, or Firm* — Louis V. Wollenberger; Joel B. German; Debra D. Condino

(57) ABSTRACT

A method for determining the optimum location for placement of an intraocular implant containing used to treat an ocular condition, particularly implants comprised of a biodegradable polymer and a therapeutic agent for the treatment of retinal tissue.

5 Claims, 10 Drawing Sheets

PREDICTED DRUG CONCENTRATIONS

AVERAGE DEXAMETHASONE SUMMATED DIFFUSION COEFFICIENTS
AH          2.41E-08 cm2/sec
Retina      1.40E-07 cm2/sec
AVERAGE FLUOCINOLONE SUMMATED DIFFUSION COEFFICIENTS  ~0.5 mg implant
AH          7.20E-09 cm2/sec
Retina      2.64E-07 cm2/sec C0          198 [ug/mL]
t           1123200 [sec]        13 days $C = C_0 \cdot (ERFC(x/(2 \cdot sqrt(D \cdot t))))$

| | x_AH [cm] | D_AH | z | C(z) [ug/ml] | x_mac [cm] | D_retina | z | C(z) [ug/g] |
|---|---|---|---|---|---|---|---|---|
| Retisert | 0.5 | 7.20E-09 | 2.78E+00 | 0.000801908 | 2.0 | 2.64E-07 | 1.83E+00 | 0.08993473 |
| Retisert (new implant site) | 0.64 | 7.20E-09 | 3.56E+00 | 0.000004603 | 1.8 | 2.64E-07 | 1.47E+00 | 0.36018978 |
| Posurdex (std needle) | 0.9 | 2.41E-08 | 2.74E+00 | 2.15E-02 | 1.4 | 1.40E-07 | 1.76E+00 | 2.49889 |
| Posurdex (.5 in. needle) | 1.3 | 2.41E-08 | 3.95E+00 | 4.45E-06 | 0.8 | 1.40E-07 | 1.01E+00 | 30.50495 |

| | x_AH [cm] | D_AH | z | C(z) [ug/ml] | x_mac [cm] | D_retina | z | C(z) [ug/g] | | Difference | Factor | |
|---|---|---|---|---|---|---|---|---|---|---|---|---|
| AH | 0.5 | 7.20E-09 | 2.780003 | 0.000802 | 2.0 | 2.6448E-07 | 1.834744 | 0.08993473 | 0 | | | |
| | 0.4 | 7.20E-09 | 2.224002 | 0.015767 | 1.9 | 2.6448E-07 | 1.743007 | 0.13016857 | 1 | 0.040233644 | 0.447367158 | 1.447367 | 0.130168572 |
| | 0.3 | 7.20E-09 | 1.668002 | 0.174122 | 1.8 | 2.6448E-07 | 1.651269 | 0.18553967 | 2 | 0.0553711 | 0.425379944 | 1.42538 | 0.185539672 |
| | 0.2 | 7.20E-09 | 1.112001 | 1.100194 | 1.7 | 2.6448E-07 | 1.559532 | 0.26047305 | 3 | 0.074933576 | 0.403867138 | 1.403867 | 0.260473048 |
| | 0.1 | 7.20E-09 | 0.556001 | 4.191052 | 1.6 | 2.6448E-07 | 1.467795 | 0.36018978 | 4 | 0.099716732 | 0.382829368 | 1.382829 | 0.36018978 |
| | 0.0 | 7.20E-09 | 0.000000 | 9.500000 | 1.5 | 2.6448E-07 | 1.376058 | 0.49067487 | 5 | 0.130485093 | 0.362267615 | 1.362268 | 0.490674873 |
| | | | | | 1.4 | 2.6448E-07 | 1.284321 | 0.65857619 | 6 | 0.167901321 | 0.342184691 | 1.342184 | 0.658576193 |
| | | | | | 1.3 | 2.6448E-07 | 1.192583 | 0.871022 | 7 | 0.212445804 | 0.322583485 | 1.322583 | 0.871021997 |
| | | | | | 1.2 | 2.6448E-07 | 1.100846 | 1.13534946 | 8 | 0.264327464 | 0.303468185 | 1.303468 | 1.135349462 |
| | | | | | 1.1 | 2.6448E-07 | 1.009109 | 1.45874728 | 9 | 0.323397823 | 0.284844 | 1.284844 | 1.458747284 |
| | | | | | 1.0 | 2.6448E-07 | 0.917372 | 1.84782156 | 10 | 0.389074277 | 0.266718082 | 1.266718 | 1.847821562 |
| | | | | | 0.9 | 2.6448E-07 | 0.825635 | 2.30810756 | 11 | 0.460285994 | 0.249096561 | 1.249097 | 2.308107555 |
| | | | | | 0.8 | 2.6448E-07 | 0.733898 | 2.84356379 | 12 | 0.535456234 | 0.231989291 | 1.231989 | 2.843563789 |
| | | | | | 0.7 | 2.6448E-07 | 0.64216 | 3.45608106 | 13 | 0.61251727 | 0.215404793 | 1.215405 | 3.45608106 |
| | | | | | 0.6 | 2.6448E-07 | 0.550423 | 4.14507701 | 14 | 0.68899596 | 0.199357578 | 1.199358 | 4.145077009 |
| | | | | | 0.5 | 2.6448E-07 | 0.458686 | 4.90718042 | 15 | 0.76210341 | 0.183857479 | 1.183857 | 4.90718042 |
| | | | | | 0.4 | 2.6448E-07 | 0.366949 | 5.73609864 | 16 | 0.828918221 | 0.168919451 | 1.168919 | 5.736098641 |
| | | | | | 0.3 | 2.6448E-07 | 0.275212 | 6.62266219 | 17 | 0.88656355 | 0.15455863 | 1.154559 | 6.62266219 |
| | | | | | 0.2 | 2.6448E-07 | 0.183474 | 7.55507562 | 18 | 0.932413429 | 0.140791332 | 1.140791 | 7.555075619 |
| | | | | | 0.1 | 2.6448E-07 | 0.091737 | 8.51936551 | 19 | 0.964289893 | 0.127634711 | 1.127635 | 8.518365513 |
| | | | | | 0.0 | 2.6448E-07 | 0 | 9.5 | 20 | 0.980834487 | 0.115106517 | 1.115107 | 9.5 |

SUMMARY @ 6 months

| | C_0 | AH [ug/mL] | Macula [ug/mL] |
|---|---|---|---|
| Retisert | 9.5 | 0.1649 | 0.0111 |
| Posurdex (std needle) | 75 | 24.5928 | 41.9594 |
| Posurdex (.5 in. needle) | 75 | 11.8205 | 55.4061 |

SUMMARY @ 3 months

| | C_0 | AH [ug/mL] | Macula [ug/mL] |
|---|---|---|---|
| Retisert | 9.5 | 0.0090 | 4.19E-05 |
| Posurdex (std needle) | 75 | 12.4863 | 30.6858 |
| Posurdex (.5 in. needle) | 75 | 3.4245 | 47.7879 |

FIG. 3

PREDICTED DRUG CONCENTRATIONS

AVERAGE DEXAMETHASONE SUMMATED DIFFUSION COEFFICIENTS
AH            2.41E-08 cm2/sec
Retina       1.40E-07 cm2/sec
AVERAGE FLUOCINOLONE SUMMATED DIFFUSION COEFFICIENTS    *0.5 mg implant
AH            7.20E-09 cm2/sec
Retina       2.64E-07 cm2/sec C0            198 [ug/mL]
t              1123200 [sec]            13 days $C = C\_0 * (\mathrm{ERFC}(x/(2*\mathrm{sqrt}(D*t))))$

| | x_AH [cm] | D_AH | z | C(z) [ug/ml] | x_mac [cm] | D_retina | z | C(z) [ug/g] |
|---|---|---|---|---|---|---|---|---|
| Retisert | 0.5 | 7.20E-09 | 2.76E+00 | 0.000801908 | 2.0 | 2.64E-07 | 1.83E+00 | 0.08993473 |
| Retisert (new implant site) | 0.64 | 7.20E-09 | 3.56E+00 | 0.000004603 | 1.6 | 2.64E-07 | 1.47E+00 | 0.36018978 |
| Posurdex (std need/e) | 0.9 | 2.41E-08 | 2.74E+00 | 2.15E-02 | 1.4 | 1.40E-07 | 1.76E+00 | 2.49883 |
| Posurdex (.5 in. needle) | 1.3 | 2.41E-08 | 3.95E+00 | 4.45E-06 | 0.8 | 1.40E-07 | 1.01E+00 | 30.50495 |

| SUMMARY @ 13 days | | | |
|---|---|---|---|
| | C_0 | AH [ug/mL] | Macula [ug/mL] |
| Retisert | 9.5 | 0.0008 | 0.0899 |
| Retisert (new implant site) | 9.5 | 0.0000 | 0.3602 |
| Posurdex (std needle) | 198 | 0.0215 | 2.5 |
| Posurdex (.5 in. needle) | 198 | 0.0000 | 30.5 |

| SUMMARY @ 6 months | | | |
|---|---|---|---|
| | C_0 | AH [ug/mL] | Macula [ug/mL] |
| Retisert | 9.5 | 0.1849 | 0.0111 |
| Posurdex (std needle) | 75 | 24.5928 | 41.9594 |
| Posurdex (.5 in. needle) | 75 | 11.8205 | 55.4061 |

| SUMMARY @ 3 months | | | |
|---|---|---|---|
| | C_0 | AH [ug/mL] | Macula [ug/mL] |
| Retisert | 9.5 | 0.0090 | 4.19E-05 |
| Posurdex (std needle) | 75 | 12.4663 | 30.6858 |
| Posurdex (.5 in. needle) | 75 | 3.4245 | 47.7879 |

FIG. 4

METHOD FOR DETERMINING OPTIMUM INTRAOCULAR LOCATIONS FOR DRUG DELIVERY SYSTEMS

CROSS-REFERENCE TO RELATED APPLICATIONS

The present application claims the benefit of U.S. Application No. 60/868,291, filed Dec. 1, 2006, the content of which in its entirety is hereby incorporated by reference.

BACKGROUND

The present invention relates to methods for determining the optimum location for placement of an intraocular drug delivery system (i.e. an implant) containing a therapeutic agent for treating an ocular condition, particularly drug delivery systems comprised of a biodegradable polymer and a therapeutic agent for the treatment of a retinal disease or condition. Additionally, the present invention relates to methods for determining the optimal amount of a therapeutic agent to load into an intraocular drug delivery device to effectively treat an ocular condition.

An ocular condition can include a disease, aliment or condition which affects or involves the eye or one of the parts or regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball. FIG. 1 is a schematic diagram of the human eye, from which it can be seen that the anterior segment is the front third of the eye (those portions of the eye in front of the vitreous humour) including the iris, cornea, ciliary body and lens. The posterior segment of the eye then contains the vitreous humour, retina, choroids and the optic nerve. FIG. 2 is a cross sectional view of the eye showing the positions of the macula (an oval yellow spot near the center of the retina, with the fovea being the center most part of the macula), retina, and retinal blood vessels.

An anterior ocular condition is a disease, ailment or condition which affects or which involves an anterior (i.e. front of the eye) ocular region or site, such as a periocular muscle, an eye lid or an eye ball tissue or fluid which is located anterior to the posterior wall of the lens capsule or ciliary muscles. Thus, an anterior ocular condition primarily affects or involves, the conjunctiva, the cornea, the conjunctiva, the anterior chamber, the iris, the posterior chamber (behind the retina but in front of the posterior wall of the lens capsule), the lens or the lens capsule and blood vessels and nerve which vascularize or innervate an anterior ocular region or site. A posterior ocular (also referred to herein synonymously as a "posterior segment") condition is a disease, ailment or condition which primarily affects or involves a posterior ocular region or site such as choroid or sclera (in a position posterior to a plane through the posterior wall of the lens capsule), vitreous, vitreous chamber, retina, optic nerve (i.e. the optic disc), and blood vessels and nerves which vascularize or innervate a posterior ocular (or posterior segment) region or site.

Thus, a posterior ocular condition can include a disease, ailment or condition, such as for example, macular degeneration (such as non-exudative age related macular degeneration and exudative age related macular degeneration); choroidal neovascularization; acute macular neuroretinopathy; macular edema (such as cystoid macular edema and diabetic macular edema); Behcet's disease, retinal disorders, diabetic retinopathy (including proliferative diabetic retinopathy); retinal arterial occlusive disease; central retinal vein occlusion; uveitis (including intermediate and anterior uveitis); retinal detachment; ocular trauma which affects a posterior ocular site or location; a posterior ocular condition caused by or influenced by an ocular laser treatment; posterior ocular conditions caused by or influenced by a photodynamic therapy; photocoagulation; radiation retinopathy; epiretinal membrane disorders; branch retinal vein occlusion; anterior ischemic optic neuropathy; non-retinopathy diabetic retinal dysfunction, retinitis pigmentosa and glaucoma. Glaucoma can be considered a posterior ocular condition because a therapeutic goal can be to prevent the loss of or reduce the occurrence of loss of vision due to damage to or loss of retinal cells or optic nerve cells (i.e. neuroprotection).

An anterior ocular condition can include a disease, ailment or condition, such as for example, aphakia; pseudophakia; astigmatism; blepharospasm; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; refractive disorders and strabismus. Glaucoma can also be considered to be an anterior ocular condition because a clinical goal of glaucoma treatment can be to reduce a hypertension of aqueous fluid in the anterior chamber of the eye (i.e. reduce intraocular pressure).

Macular edema is a condition characterized by thickening and swelling of the macula of the eye, often caused by the collection of fluids and protein on or under the macula. This condition can significantly impair vision, such as by distorting the patient's central vision since the macula is near the center of the retina at the back of the eye. Macular edema is a major cause of visual loss in patients with diabetes, central retinal vein occlusion (CRVO) and branch retinal vein occlusion (BRVO). Although laser photocoagulation can reduce further vision loss in patients with diabetic macular edema (DME), vision that has already been decreased by macular edema usually does not improve by use of laser photocoagulation. Currently, there is no FDA (U.S. Food and Drug Administration) approved treatment for macular edema associated with CRVO. For macular edema associated with BRVO, grid laser photocoagulation may be an effective treatment for some patients.

Diabetic macular edema results from abnormal leakage of macromolecules, such as lipoproteins, from retinal capillaries into the extravascular space followed by an oncotic influx of water into the extravascular space. Abnormalities in the retinal pigment epithelium may also cause or contribute to diabetic macular edema. These abnormalities can allow increased fluid from the choriocapillaries to enter the retina or they may decrease the normal efflux of fluid from the retina to the choriocapillaries. The mechanism of breakdown of the blood-retina barrier at the level of the retinal capillaries and the retinal pigment epithelium may be due to changes to tight junction proteins such as occludin. Antcliff R., et al Marshall J., *The pathogenesis of edema in diabetic maculopathy*, Semin Opthalmol 1999; 14:223-232.

Macular edema from venous occlusive disease can result from thrombus formation at the lamina cribrosa or at an arteriovenous crossing. These changes can result in an increase in retinal capillary permeability and accompanying retinal edema. The increase in retinal capillary permeability and subsequent retinal edema can ensue from of a breakdown of the blood retina barrier mediated in part by vascular endothelial growth factor (VEGF), a 45 kD glycoprotein, as it is known that VEGF can increase vascular permeability. VEGF may regulate vessel permeability by increasing phosphorylation of tight junction proteins such as occludin and zonula occluden. Similarly, in human non-ocular disease states such as ascites, VEGF has been characterized as a potent vascular permeability factor (VPF).

Damage to the optic nerve can be due to increased pressure in the eye (i.e. elevated intraocular pressure). Elevated intraocular pressure (IOP) (ocular hypertension) can result from excess aqueous humor accumulating because the eye either produces too much or drains too little aqueous humor.

It is known to make and use an intraocular implant to treat an ocular condition. See for example U.S. Pat. Nos. 4,521,210; 4,853,224; 4,997,652; 5,164,188; 5,443,505; 5,766,242; 5,824,072; 5,869,079; 6,331,313; 6,726,918; 6,699,493; 5,501,856; 6,074,661; and; 6,369,116, and U.S. patent application Ser. Nos. 11/070,158; 11/292,544; 10/966,764; 11/117,879; 11/119,463; 11/116,698; 11/119,021; 11/118,519; 11/119,001; 11/118,288; 11/119,024; 10/340,237; 10/837,357; 10/837,355; 10/837,142; 10/837,356; 10/836,911; 10/837,143; 10/837,260; 10/837,379; 10/836,880, and 10/918,597, each of which is hereby incorporated by reference.

U.S. Pat. No. 6,713,081 discloses ocular implant devices made from polyvinyl alcohol and used for the delivery of a therapeutic agent to an eye in a controlled and sustained manner. The implants may be placed subconjunctivally or intravitreally in an eye. Devices for ocular implantation are also known, such as those described in U.S. Pat. No. 6,899,717; U.S. Pat. No. 7,090,681; US 2005 0203542 and US 2005 0154399. Each of these publications is hereby incorporated by reference.

Various treatments are known for the treatment of retinal diseases, including macular edema from diabetic retinopathy, venous occlusive disease and uveitis, such as treatment with corticosteroid implants. Unfortunately, known implants have been placed in the vitreous to treat an ocular condition in a somewhat haphazard manner. Thus, if an implant is inserted into the anterior vitreous (i.e. in proximity to the cilliary body and trabecular meshwork) elevated intraocular pressure and a high incidence of cataract can result. For example, drug (therapeutic agent) exposure to the anterior segment can lead to myocilin accumulation in the trabecular meshwork cells, leading to undesired elevation in intraocular pressure (10P). On the other hand, placing the implant in the posterior vitreous can deliver an excess of the therapeutic agent contained by the implant to the target retinal tissues.

A recent study has shown that invitreal treatment with Kenalog® (4 mg triamcinalone) can result in about 15 to 30% of the patients at 6 months having IOP of ≥10 mm Hg. Additionally, treatment with intravitreal Retisert™ (about 120 or 480 µg of fluocinolone) released over 8 months or longer can result in 59% of patients having IOP increase of a ≥10 mm HG. Furthermore, treatment with intravitreal POSURDEX® (700 µg dexamethasone released over about 1 to 2 months) can result in about 15% of patients having an IOP increase of a ≥10 mm Hg. (see Jaffe et al, *Ophthalmology*, 2006; 113: 1020-1027). Determination of an optimal intravitreal implant placement location and/or the amount of therapeutic agent to load in the implant may permit reduction or elimination of these undesirable side effects subsequent to intravitreal administration of a drug delivery system.

What is needed therefore is a method for determining the optimal location for an intraocular implant which can deliver a therapeutically effective amount of an active agent to the desired tissue (e.g. retinal tissue) over a sustained period without causing undesirable side effects or with reduced side effects.

DRAWINGS

FIGS. 1 and 2 are schematic representations of the human eye.

FIGS. 3-4 present results from the predicted drug concentration analysis according to the invention.

SUMMARY

Figure 1:
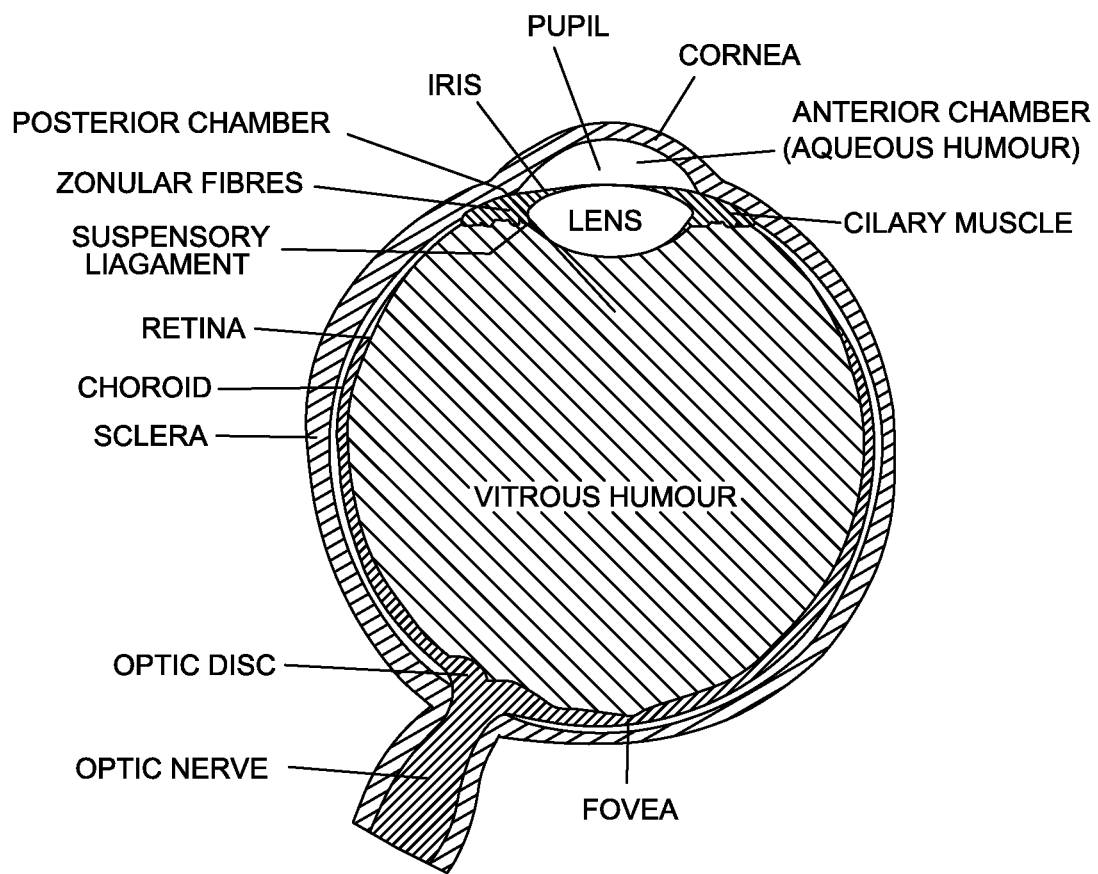
Figure 2:
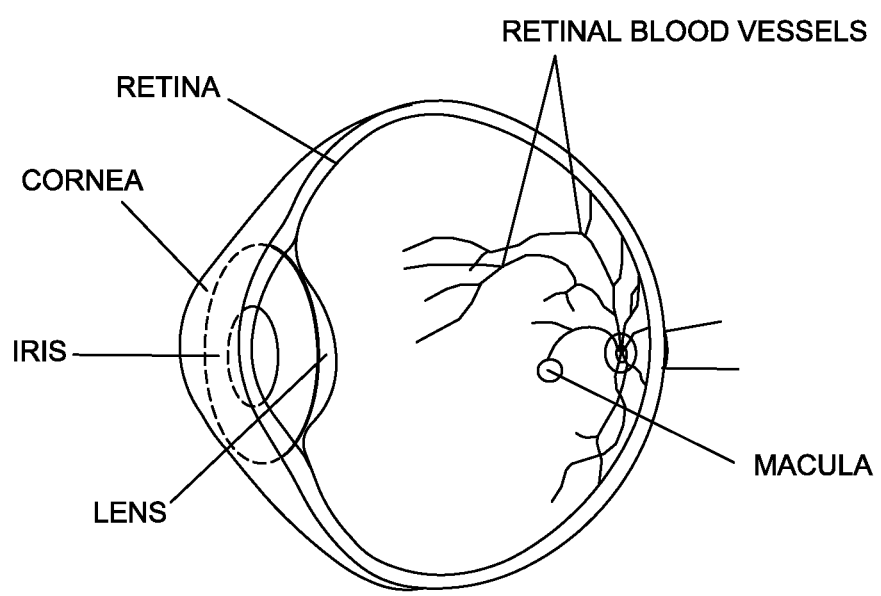

The present invention meets this need by providing a method for determining the optimum location for placement of an intraocular implant containing a therapeutic agent used to treat an ocular condition, particularly implants comprised of a biodegradable polymer and a therapeutic agent for the treatment of a condition of retinal tissue.

DETAILED DESCRIPTION OF THE INVENTION

Definitions

As used herein, the words or terms set forth below have the meanings shown.

"About" means that the item, parameter or term so qualified encompasses a range of plus or minus ten percent above and below the value of the stated item, parameter or term.

"Administration", or "to administer" means the step of giving (i.e. administering) a pharmaceutical composition to a subject. The pharmaceutical compositions disclosed herein can be "locally administered", that is administered at or in the vicinity of the site at which a therapeutic result or outcome is desired. For example to treat an ocular condition (such as for example glaucoma, a macular edema, uveitis or macular degeneration) intravitreal injection or implantation of a sustained release device such as active agent containing polymeric implant can be carried out. "Sustained release" means release of an active agent (such as a vasoactive agent) over a period of at least about five to seven days and for as long as several years.

"Associated with" means mixed with, dispersed within, coupled to, covering, or surrounding.

"Biodegradable polymer" means a polymer or polymers which degrade in vivo, and wherein erosion of the polymer or polymers over time occurs concurrent with or subsequent to release of the therapeutic agent. Specifically, hydrogels such as methylcellulose which act to release drug through polymer swelling are specifically excluded from the term "biodegradable polymer". The terms "biodegradable" and "bioerodible" are equivalent and are used interchangeably herein. A biodegradable polymer may be a homopolymer, a copolymer, or a polymer comprising more than two different polymeric units.

"Entirely free" (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Intraocular implant" means a device or element that is structured, sized, or otherwise configured to be placed in an eye. Intraocular implants are generally biocompatible with physiological conditions of an eye and do not cause unacceptable adverse side effects. Intraocular implants can be placed in an eye without disrupting vision of the eye.

"Pharmaceutical composition" (synonymously a composition) is a formulation that contains at least one active ingredient as well as, for example, one or more excipients, buffers, carriers, stabilizers, preservatives and/or bulking agents, and is suitable for administration to a patient to achieve a desired effect or result means a formulation in which an active ingredient (the active agent) can be a vasoactive agent, such as a vasodilator.

"Substantially free" means present at a level of less than one percent by weight of the pharmaceutical composition.

"Therapeutic component" means a portion of an intraocular implant comprising one or more therapeutic agents or substances used to treat a medical condition of the eye. The therapeutic component may be a discrete region of an intraocular implant, or it may be homogenously distributed throughout the implant. The therapeutic agents of the therapeutic component are typically ophthalmically acceptable, and are provided in a form that does not cause adverse reactions when the implant is placed in an eye.

"Therapeutically effective amount" means the level or amount of agent needed to treat an ocular condition, or reduce or prevent ocular injury or damage without causing significant negative or adverse side effects to the eye or a region of the eye.

"Treat", "treating", or "treatment" means reduction or resolution or prevention of an ocular condition, ocular injury or damage, or to promote healing of injured or damaged ocular tissue.

Drug Delivery Systems Useful with the Invention

The present invention provides a method for determining the optimal location in the eye for implantation/placement of a drug delivery system, for extended or sustained drug release into the eye tissue to best achieve one or more desired therapeutic effects, while avoiding or decreasing undesirable side effects, such as an increased IOP. Additionally, the present invention also provides a method for determining the optimal amount of a therapeutic agent to load into a drug delivery device (such an implant) intended for intravitreal administration at a particular intravitreal location in order to effectively treat an ocular condition (such as a retinal disease or condition) with little or no side effects. The drug delivery systems are in the form of implants or implant elements that may be placed in an eye and can be of various types, including known implants for the treatment of ocular conditions.

Intraocular drug delivery systems useful with the method of the invention can comprise a therapeutic component (i.e. a therapeutic agent or drug) and a drug release sustaining component (i.e. a polymeric carrier) associated with the therapeutic component. In accordance with the present invention, the therapeutic component comprises, consists essentially of, or consists of, a therapeutic agent useful for treating an ocular condition, such as macular edema. The drug release sustaining component is associated with the therapeutic component to sustain release of an amount of the therapeutic agent into an eye in which the implant is placed. The amount of the therapeutic agent is released into the eye for a period of time greater than about one week after the implant is placed in the eye and is effective in reducing or treating an ocular condition (such as glaucoma, or macular edema) to improve or maintain vision of an eye of a patient.

The drug release sustaining component (which is associated with the therapeutic component) can be a polymer such as a biodegradable polymer or polymer matrix For example, the matrix may comprise a polymer selected from the group consisting of polylactides, poly (lactide-co-glycolides), polycaprolactones, and combinations thereof.

The biodegradable polymer of the implant can be for example a polylactides (PLA), polyglycolide (PGA), poly (lactide co-glycolide (PLGA), polycaprolactone, polyanhydride, poly methyl vinyl ether maleic anhydride, polycarbonates, polyarylates, polydioxanone, polyhydroxyalkanoates, and chitosan.

The drug delivery system can be an implant, microsphere, capsule, tablet, fiber, rod, filament, disc and the like. A drug delivery system, such as an implant, can be structured to be placed in the vitreous of the eye, the implant of can be formed as a rod, a wafer, or a particle and the implant can be made by an extrusion process.

The implant can be placed in the posterior of the eye, for example using a trocar or a 25-30 gauge syringe. Alternately, the implant can be intravitreally administered using one or more of the applicators shown in related U.S. patents and published U.S. Pat. Nos. 6,899,717; 7,090,681; 2005 0203542, and; 2005 01543399. The applicator can comprise a needle with a canula which contains the implant.

Finally, the present invention also encompasses a method to preventing vision loss by intraocular placement of an intraocular implant comprising a therapeutic agent and a carrier.

In one embodiment of the present invention, an intraocular implant comprises a biodegradable polymer matrix. The biodegradable polymer matrix is one type of a drug release sustaining component. The biodegradable polymer matrix is effective in forming a biodegradable intraocular implant. The biodegradable intraocular implant comprises a therapeutic agent associated with the biodegradable polymer matrix. The matrix degrades at a rate effective to sustain release of an amount of the therapeutic agent for a time greater than about one week from the time in which the implant is placed in ocular region or ocular site, such as the vitreous of an eye.

The therapeutic agent can be a corticosteriod, an aminoglycoside or an anti-VEGF antibody such as set forth in published U.S. patent application 2006 0182783, publish Aug. 17, 2006.

Useful implants can also include salts of the disclosed therapeutic agents. Pharmaceutically acceptable acid addition salts of the compounds of the invention are those formed from acids which form non-toxic addition salts containing pharmaceutically acceptable anions, such as the hydrochloride, hydrobromide, hydroiodide, sulfate, or bisulfate, phosphate or acid phosphate, acetate, maleate, fumarate, oxalate, lactate, tartrate, citrate, gluconate, saccharate and p-toluene sulphonate salts.

The therapeutic agent may be in a particulate or powder form and entrapped by the biodegradable polymer matrix. Usually, therapeutic agent particles in intraocular implants will have an effective average size less than about 3000 nanometers. In certain implants, the particles may have an effective average particle size about an order of magnitude smaller than 3000 nanometers. For example, the particles may have an effective average particle size of less than about 500 nanometers. In additional implants, the particles may have an effective average particle size of less than about 400 nanometers, and in still further embodiments, a size less than about 200 nanometers.

The therapeutic agent of the implant is preferably from about 10% to 90% by weight of the implant. More preferably, the therapeutic agent is from about 20% to about 80% by weight of the implant. In a preferred embodiment, the therapeutic agent comprises about 40% by weight of the implant (e.g., 30%-50%). In another embodiment, the therapeutic agent comprises about 60% by weight of the implant.

Suitable polymeric materials or compositions for use in the implant include those materials which are compatible, that is biocompatible, with the eye so as to cause no substantial interference with the functioning or physiology of the eye.

Such materials preferably are at least partially and more preferably substantially completely biodegradable or bioerodible.

Examples of useful polymeric materials include, without limitation, such materials derived from and/or including organic esters and organic ethers, which when degraded result in physiologically acceptable degradation products, including the monomers. Also, polymeric materials derived from and/or including, anhydrides, amides, orthoesters and the like, by themselves or in combination with other monomers, may also find use. The polymeric materials may be addition or condensation polymers, advantageously condensation polymers. The polymeric materials may be cross-linked or non-cross-linked, for example not more than lightly cross-linked, such as less than about 5%, or less than about 1% of the polymeric material being cross-linked. For the most part, besides carbon and hydrogen, the polymers will include at least one of oxygen and nitrogen, advantageously oxygen. The oxygen may be present as oxy, e.g. hydroxy or ether, carbonyl, e.g. non-oxo-carbonyl, such as carboxylic acid ester, and the like. The nitrogen may be present as amide, cyano and amino. The polymers set forth in Heller, Biodegradable Polymers in Controlled Drug Delivery, In: CRC Critical Reviews in Therapeutic Drug Carrier Systems, Vol. 1, CRC Press, Boca Raton, Fla. 1987, pp 39-90, which describes encapsulation for controlled drug delivery, can find use in the present implants.

Of additional interest are polymers of hydroxyaliphatic carboxylic acids, either homopolymers or copolymers, and polysaccharides. Polyesters of interest include polymers of D-lactic acid, L-lactic acid, racemic lactic acid, glycolic acid, polycaprolactone, and combinations thereof. Generally, by employing the L-lactate or D-lactate, a slowly eroding polymer or polymeric material is achieved, while erosion is substantially enhanced with the lactate racemate.

Among the useful polysaccharides are, without limitation, calcium alginate, and functionalized celluloses, particularly carboxymethylcellulose esters characterized by being water insoluble, a molecular weight of about 5 kD to 500 kD, for example.

Other polymers of interest include, without limitation, polyesters, polyethers and combinations thereof which are biocompatible and may be biodegradable and/or bioerodible.

Some preferred characteristics of the polymers or polymeric materials for use in the present invention may include biocompatibility, compatibility with the therapeutic component, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Equally important to controlling the biodegradation of the polymer and hence the extended release profile of the implant is the relative average molecular weight of the polymeric composition employed in the implant. Different molecular weights of the same or different polymeric compositions may be included in the implant to modulate the release profile. In certain implants, the relative average molecular weight of the polymer will range from about 9 to about 64 kD, usually from about 10 to about 54 kD, and more usually from about 12 to about 45 kD.

In some implants, copolymers of glycolic acid and lactic acid are used, where the rate of biodegradation is controlled by the ratio of glycolic acid to lactic acid. The most rapidly degraded copolymer has roughly equal amounts of glycolic acid and lactic acid. Homopolymers, or copolymers having ratios other than equal, are more resistant to degradation. The ratio of glycolic acid to lactic acid will also affect the brittleness of the implant, where a more flexible implant is desirable for larger geometries. The % of polylactic acid in the polylactic acid polyglycolic acid (PLGA) copolymer can be 0-100%, preferably about 15-85%, more preferably about 35-65%. In some implants, a 50/50 PLGA copolymer is used.

The biodegradable polymer matrix of the intraocular implant may comprise a mixture of two or more biodegradable polymers. For example, the implant may comprise a mixture of a first biodegradable polymer and a different second biodegradable polymer. One or more of the biodegradable polymers may have terminal acid groups.

Release of a drug from an erodible polymer is the consequence of several mechanisms or combinations of mechanisms. Some of these mechanisms include desorption from the implants surface, dissolution, diffusion through porous channels of the hydrated polymer and erosion. Erosion can be bulk or surface or a combination of both. As discussed herein, the matrix of the intraocular implant may release drug at a rate effective to sustain release of an amount of the therapeutic agent for more than one week after implantation into an eye. In certain implants, therapeutic amounts of the therapeutic agent are released for more than about one month, and even for about six months or more.

The release of the therapeutic agent from the intraocular implant comprising a biodegradable polymer matrix may include an initial burst of release followed by a gradual increase in the amount of the therapeutic agent released, or the release may include an initial delay in release of the therapeutic agent followed by an increase in release. When the implant is substantially completely degraded, the percent of the therapeutic agent that has been released is about one hundred. Compared to existing implants, the implants disclosed herein do not completely release, or release about 100% of the therapeutic agent, until after about one week of being placed in an eye.

It may be desirable to provide a relatively constant rate of release of the therapeutic agent from the implant over the life of the implant. For example, it may be desirable for the therapeutic agent to be released in amounts from about 0.01 µg to about 2 µg per day for the life of the implant. However, the release rate may change to either increase or decrease depending on the formulation of the biodegradable polymer matrix. In addition, the release profile of the therapeutic agent may include one or more linear portions and/or one or more non-linear portions. Preferably, the release rate is greater than zero once the implant has begun to degrade or erode.

The implants may be monolithic, i.e. having the active agent or agents homogenously distributed through the polymeric matrix, or encapsulated, where a reservoir of active agent is encapsulated by the polymeric matrix. Due to ease of manufacture, monolithic implants are usually preferred over encapsulated forms. However, the greater control afforded by the encapsulated, reservoir-type implant may be of benefit in some circumstances, where the therapeutic level of the drug falls within a narrow window. In addition, the therapeutic component, including the therapeutic agent(s) described herein, may be distributed in a non-homogenous pattern in the matrix. For example, the implant may include a portion that has a greater concentration of the therapeutic agent relative to a second portion of the implant.

The intraocular implants disclosed herein may have a diameter size of between about 0.4 mm and about 12 mm, or between about 0.4 mm and about 10 mm for administration with a needle applicator. The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. Or the implant may be a cylindrical pellet with a length of about 7 mm to about 10 mm, and a diameter of about 0.75 mm to about 1.5 mm.

The implants may also be at least somewhat flexible so as to facilitate both insertion of the implant in the eye, such as in the vitreous, and accommodation of the implant. The total weight of the implant is usually about 250-5000 µg, more preferably about 500-1000 µg. For example, an implant may be about 500 µg, or about 1000 µg. For non-human individuals, the dimensions and total weight of the implant(s) may be larger or smaller, depending on the type of individual. For example, humans have a vitreous volume of approximately 3.8 ml, compared with approximately 30 ml for horses, and approximately 60-100 ml for elephants. An implant sized for use in a human may be scaled up or down accordingly for other animals, for example, about 8 times larger for an implant for a horse, or about, for example, 26 times larger for an implant for an elephant.

Thus, implants can be prepared where the center may be of one material and the surface may have one or more layers of the same or a different composition, where the layers may be cross-linked, or of a different molecular weight, different density or porosity, or the like. For example, where it is desirable to quickly release an initial bolus of drug, the center may be a polylactate coated with a polylactate-polyglycolate copolymer, so as to enhance the rate of initial degradation. Alternatively, the center may be polyvinyl alcohol coated with polylactate, so that upon degradation of the polylactate exterior the center would dissolve and be rapidly washed out of the eye.

The implants may be of any geometry including fibers, sheets, films, microspheres, spheres, circular discs, plaques and the like. The upper limit for the implant size will be determined by factors such as toleration for the implant, size limitations on insertion, ease of handling, etc. Where sheets or films are employed, the sheets or films will be in the range of at least about 0.5 mm×0.5 mm, usually about 3-10 mm×5-10 mm with a thickness of about 0.1-1.0 mm for ease of handling. Where fibers are employed, the fiber diameter will generally be in the range of about 0.05 to 3 mm and the fiber length will generally be in the range of about 0.5-10 mm. Spheres may be in the range of about 0.5 µm to 4 mm in diameter, with comparable volumes for other shaped particles.

The size and form of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

The proportions of therapeutic agent, polymer, and any other modifiers may be empirically determined by formulating several implants with varying proportions. A USP approved method for dissolution or release test can be used to measure the rate of release (USP 23; NF 18 (1995) pp. 1790-1798). For example, using the infinite sink method, a weighed sample of the implant is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

In addition to the therapeutic agent included in the intraocular implants disclosed hereinabove, the intraocular implants may also include one or more additional ophthalmically acceptable therapeutic agents. For example, the implant may include one or more antihistamines, one or more different antibiotics, one or more beta blockers, one or more steroids, one or more antineoplastic agents, one or more immunosuppressive agents, one or more antiviral agents, one or more antioxidant agents, and mixtures thereof.

Pharmacologic or therapeutic agents which may find use in the present systems, include, without limitation, those disclosed in U.S. Pat. Nos. 4,474,451, columns 4-6 and 4,327,725, columns 7-8.

The amount of active agent or agents employed in the implant, individually or in combination, will vary widely depending on the effective dosage required and the desired rate of release from the implant. As indicated herein, the agent will be at least about 1, more usually at least about 10 weight percent of the implant, and usually not more than about 80, more usually not more than about 40 weight percent of the implant.

In addition to the therapeutic component, the intraocular implants disclosed herein may include effective amounts of buffering agents, preservatives and the like. Suitable water soluble buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents advantageously present in amounts sufficient to maintain a pH of the system of between about 2 to about 9 and more preferably about 4 to about 8. As such the buffering agent may be as much as about 5% by weight of the total implant. Suitable water soluble preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof. These agents may be present in amounts of from 0.001 to about 5% by weight and preferably 0.01 to about 2% by weight.

In addition, the implants may include a solubility enhancing component provided in an amount effective to enhance the solubility of the therapeutic agent relative to substantially identical implants without the solubility enhancing component. For example, an implant may include a β-cyclodextrin, which is effective in enhancing the solubility of the therapeutic agent. The β-cyclodextrin may be provided in an amount from about 0.5% (w/w) to about 25% (w/w) of the implant. In certain implants, the β-cyclodextrin is provided in an amount from about 5% (w/w) to about 15% (w/w) of the implant In some situations mixtures of implants may be utilized employing the same or different pharmacological agents. In this way, a cocktail of release profiles, giving a biphasic or triphasic release with a single administration is achieved, where the pattern of release may be greatly varied.

Additionally, release modulators such as those described in U.S. Pat. No. 5,869,079 may be included in the implants. The amount of release modulator employed will be dependent on the desired release profile, the activity of the modulator, and on the release profile of the therapeutic agent in the absence of modulator. Electrolytes such as sodium chloride and potassium chloride may also be included in the implant. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

Various techniques may be employed to produce the implants described herein. Useful techniques include, but are not necessarily limited to, solvent evaporation methods, phase separation methods, interfacial methods, molding methods, injection molding methods, extrusion methods, co-extrusion methods, carver press method, die cutting methods, heat compression, combinations thereof and the like.

Specific methods are discussed in U.S. Pat. No. 4,997,652. Extrusion methods may be used to avoid the need for solvents in manufacturing. When using extrusion methods, the polymer and drug are chosen so as to be stable at the temperatures required for manufacturing, usually at least about 85 degrees Celsius. Extrusion methods use temperatures of about 25 degrees C. to about 150 degrees C., more preferably about 65 degrees C. to about 130 degrees C. An implant may be produced by bringing the temperature to about 60 degrees C. to about 150 degrees C. for drug/polymer mixing, such as about 130 degrees C., for a time period of about 0 to 1 hour, 0 to 30 minutes, or 5-15 minutes. For example, a time period may be about 10 minutes, preferably about 0 to 5 min. The implants are then extruded at a temperature of about 60 degrees C. to about 130 degrees C., such as about 75 degrees C.

In addition, the implant may be coextruded so that a coating is formed over a core region during the manufacture of the implant.

Compression methods may be used to make the implants, and typically yield implants with faster release rates than extrusion methods. Compression methods may use pressures of about 50-150 psi, more preferably about 70-80 psi, even more preferably about 76 psi, and use temperatures of about 0 degrees C. to about 115 degrees C., more preferably about 25 degrees C.

The implants of the present invention may be inserted into the eye, for example the vitreous chamber of the eye, by a variety of methods, including placement by forceps or by trocar following making a 2-3 mm incision in the sclera. One example of a device that may be used to insert the implants into an eye is disclosed in U.S. Patent Publication No. 2004/0054374. The method of placement may influence the therapeutic component or drug release kinetics. For example, delivering the implant with a trocar may result in placement of the implant deeper within the vitreous than placement by forceps, which may result in the implant being closer to the edge of the vitreous. The location of the implant may influence the concentration gradients of therapeutic component or drug surrounding the element, and thus influence the release rates (e.g., an element placed closer to the edge of the vitreous may result in a slower release rate).

The implants used with the method of the invention may also be configured to release additional therapeutic agents, as described above. The implants can be used to treat a variety of ocular conditions including:

Glaucoma, maculopathies/retinal degeneration: macular degeneration, including age related macular degeneration (ARMD), such as non-exudative age related macular degeneration and exudative age related macular degeneration, choroidal neovascularization, retinopathy, including diabetic retinopathy, acute and chronic macular neuroretinopathy, central serous chorioretinopathy, and macular edema, including cystoid macular edema, and diabetic macular edema. Uveitis/retinitis/choroiditis: acute multifocal placoid pigment epitheliopathy, Behcet's disease, birdshot retinochoroidopathy, infectious (syphilis, lyme, tuberculosis, toxoplasmosis), uveitis, including intermediate uveitis (pars planitis) and anterior uveitis, multifocal choroiditis, multiple evanescent white dot syndrome (MEWDS), ocular sarcoidosis, posterior scleritis, serpignous choroiditis, subretinal fibrosis, uveitis syndrome, and Vogt-Koyanagi-Harada syndrome. Vascular diseases/exudative diseases: retinal arterial occlusive disease, central retinal vein occlusion, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angitis, sickle cell retinopathy and other hemoglobinopathies, angioid streaks, familial exudative vitreoretinopathy, Eales disease. Traumatic/surgical: sympathetic ophthalmic, uveitic retinal disease, retinal detachment, trauma, laser, PDT, photocoagulation, hypoperfusion during surgery, radiation retinopathy, bone marrow transplant retinopathy. Proliferative disorders: proliferative vitreal retinopathy and epiretinal membranes, proliferative diabetic retinopathy. Infectious disorders: ocular histoplasmosis, ocular toxocariasis, presumed ocular histoplasmosis syndrome (POHS), endophthalmitis, toxoplasmosis, retinal diseases associated with HIV infection, choroidal disease associated with HIV infection, uveitic disease associated with HIV Infection, viral retinitis, acute retinal necrosis, progressive outer retinal necrosis, fungal retinal diseases, ocular syphilis, ocular tuberculosis, diffuse unilateral subacute neuroretinitis, and myiasis. Genetic disorders: retinitis pigmentosa, systemic disorders with associated retinal dystrophies, congenital stationary night blindness, cone dystrophies, Stargardt's disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, pseudoxanthoma elasticum. Retinal tears/holes: retinal detachment, macular hole, giant retinal tear. Tumors: retinal disease associated with tumors, congenital hypertrophy of the RPE, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, intraocular lymphoid tumors. Miscellaneous: punctate inner choroidopathy, acute posterior multifocal placoid pigment epitheliopathy, myopic retinal degeneration, acute retinal pigment epithelitis and the like.

Method of Determining Optimal Location for Intraocular Drug Delivery System

Intravitreal sustained-release implants are generally placed in the anterior vitreous to treat macular diseases, such as diabetic macular edema, and diffuse retinal diseases such as retinitis pigmentosa. Periocular administration of medications in the sub-Tenon's space or in the orbital floor is often performed without specific regard to the location of the disease. The present inventors sought to develop a method to optimize the location of ocular implants to best treat ocular conditions. In particular, the present inventors sought to determine how best to treat macular edema with corticosteroid-releasing ocular implants, while limiting IOP elevation, and have determined that the best method is to maximize macular drug exposure and reduce or minimize the anterior segment exposure of the corticosteroid (both the duration and the dose).

Fick's Second Law of Diffusion was developed by Adolf Fick in about 1855. It is a diffusion equation to explain the behavior of non-steady state diffusion, i.e. diffusion that change with time. Fick's Second Law is as follows:

$$\frac{\partial C}{\partial t} = D \frac{\partial^2 C}{\partial x^2}$$

Boundary Conditions:

$$C(x, 0) = 0$$
$$C(0, t) = C_0$$
$$C(\eta) = C_0 \left[ 1 - \frac{2}{\sqrt{\pi}} \int_0^\eta e^{-s^2} ds \right] \equiv C_0[1 - \mathrm{erf}(\eta)] \equiv C_0 \mathrm{erfc}(\eta)$$
$$\eta = \frac{x}{2(Dt)^{1/2}}$$
$$C(x, t) = C_0 \mathrm{erfc}\left[ x / \left( 2\sqrt{Dt} \right) \right]$$

$C_o$=constant concentration in the tissue adjacent to the source (implant)
D=the coefficient for solution diffusion through the tissue
t=time
erfc=complementary error function
x=distance between the source and the measurement position.

The inventors used a solution to Fick's $2^{nd}$ Law to understand, predict and analyze the ocular distribution of drugs released from implants. According to the invention, diffusion of drug can be predicted with the following solution to Fick's Second Law:

$$C = C_o \mathrm{erfc}[x/(2\sqrt{Dt})]$$

$C_o$ is the drug concentration in the tissue adjacent to the source (implant),
D is the coefficient for solution diffusion through the vitreous,
t is time,
erfc is the complementary error function,
x is the distance between the implant and the measurement position (i.e. macula),
and C is the drug concentration at the measurement position.

The inventors used the 2 boundary conditions to solve for the solution C(x,t). The first boundary condition, C(x, 0)=0, means that initially (time=0 seconds), there is no drug anywhere. The other boundary condition, C(0, t)=$C_0$, means that at any time point, the concentration at the implant site is $C_0$.

The present inventors have thereby understood that the drug concentrations in the ocular tissues, such as the retina, closest to an intravitreal implant would be highest, and more therapeutic, compared with drug concentrations away from the implant. Therefore, the ideal position for a diffusion-based vitreous implant to treat macular diseases would be in the posterior half of the vitreous cavity, preferably away from the visual axis. Using this approach, a corticosteroid-eluting implant will result in higher drug concentrations in the macula, and in addition, lower drug concentrations will result in the anterior segment which will reduce the risk of corticosteroid-induced ocular hypertension.

To treat diffuse retinal diseases, such as retinitis pigmentosa, an implant located more centrally in the vitreous cavity, slightly below fixation, will result in a more equal distribution of drug throughout the retina. C can be influenced by the drug concentrations immediately around the implant ($C_o$) and this is most affected by the implant release rate. In the case of an implant placed in the posterior vitreous to treat macular diseases, increase drug concentrations to the macula will be expected by increasing the release rate of the implant. Preferred implant release rates will depend on the potency of the drug but generally range in the 0.1 to 15 microgram per day. The amount of drug loading in the implant will influence the duration of release. Implants weighing greater that 0.5 to 1 milligram may not stay suspended well in the vitreous cavity to delivery drug to the macula. Therefore, vitreous implants that require greater drugs loads should be segmented such that they will not sink in the vitreous cavity and lay on the inferior retinal surface. For example, if the required drug load plus polymer combination in a bioerodible implant system is 2 milligram in weight and 6 millimeter long, the implant should be injected into the vitreous in a total of 3 segments, each weighing approximately 0.66 milligram and measuring 2 millimeter in length.

The charge of the drug released from the vitreous implant can also influence the clearance pathway from the eye. For example, cationic drugs, such as the aminoglycosides, are not well eliminated across the retina and have a preferred elimination anteriorly though the trabecular meshwork. In contrast, anionic compounds, such as the fluoroquinilones, favor trans-retinal elimination and anterior segment exposure is minimized. Therefore, the drug charge can be manipulated to influence ocular drug distribution. The molecular weight of the drug can also influence the elimination from the eye. In general terms, drugs less than 40 KD can be delivered through the retina, 40 to 70 KD compounds are intermediate between clearance interiorly vs. posteriorly, and drugs between 70 and 155 KD are generally eliminated anteriorly. An exception to the latter are drugs that are in high concentrations at the retinal interface, that can overcome the barriers such as the internal limiting membrane and the plexiform layers. Mueller cell transport may also facilitate macromolecule transit through the retina. Therefore, drugs, such as anti-VEGF monoclonal antibodies with molecular weights approximately 150 KD, can be transported to the subretinal space to treat choroidal neovascularization after release from a vitreous implant assuming the concentrations gradients are sufficient at the retinal interface.

The relationship of molecular weight (MW) to diffusion is discussed in Kim et al, *Controlled Drug Release from an Ocular Implant: An Evaluation Using Dynamic Three-Dimensional Magnetic Resonance Imaging*, Investigative Opthalmology & Visual Science, August 2004, Vol. 45, No. 8, wherein page 2728, discusses the Peclet number (convection/diffusion ration), where high numbers (with high MW compounds) mean transport by convection currents, low numbers mean transport by diffusion, typical of low MW compounds Thus, in another aspect of the invention, compounds that are high MW, such as Fabs and monoclonal antibodies, move with low velocity in the vitreous and depend nearly solely on the convection currents to be delivered to the retina. Once at the retinal interface, there is some dependence on Muller cells to transport the compounds to the posterior retina/subretinal space. Thus, a location for a drug delivery system, especially those that are of high MW, would be very close to the retina, in the case of subfoveal choroidal neovascularization, the DDS should be in close approximation to the macula. Thus, in accordance with the present invention, implants can be appropriately positioned in the optimal location of the eye to maximize efficacy and minimize potential adverse effects; whereas, previous implants that must be maintained at the pars plana will not be able to give you this improved result.

The lipophilicity of a drug released from a vitreous implant, such as those with LogP values over 2 to 3, favors transretinal elimination, and there can also be significant partitioning into the retina that may be of therapeutic value.

The movement of drugs to the retina released from implants placed in the subconjunctival, intrascleral, or suprachoroidal space cannot be simply explained by the above equation since there are significant clearance mechanisms that ultimately reduce C. Transscleral drug delivery is impacted by drug clearance occurring through blood vessels (conjunctiva and choroid) and by the conjunctival lymphatics. Counter directional convection flow of fluids, such as those that occur with uveoscleral flow, and the flow generated from the hydrostatic and osmotic pressure differences between the vitreous cavity and choroid, can also have an impact on the transscleral movement of drugs. Metabolic enzymes and transporter proteins in the choroid and RPE can also impact the transit of drugs in the region. Drugs with lower molecular weights, preferably <1000 KD, higher log P, and neutral charge, facilitate transscleral delivery to the retina. Since the venous blood flow in the choroid is significantly higher than that of the ciliary body, drugs released from implants in the subconjunctival, intrascleral, or suprachoroidal space can enter into the ciliary body region and anterior chamber with greater facility. This may be an advantage when treating diseases such as glaucoma. The best location of implants in the subconjunctival, intrascleral, or suprachoroidal space will depend on the disease being treated. Implants located more posteriorly will facilitate treating macular diseases and implants positioned more anteriorly will facilitate delivery of drug to the anterior segment. Since there are significant clearance mechanisms that inhibit the transscleral movement of drugs, a compensatory increase in the implant release rate is required to effectively deliver drug to the retina, generally in the range of 1 log unit higher than that of a vitreous implant.

EXAMPLE

The following non-limiting Example is presented to exemplify aspects of the present invention.

Example 1

Based on several known intraocular drug delivery systems, the present inventors determined the concentrations of the respective active therapeutic agents for different drug delivery system positions, specifically the macula and anterior humour concentrations. Those drug delivery systems comprised the therapeutic agents dexamethasone and fluocinolone. These drug delivery systems are utilized for the treatment of ocular conditions, specifically macula edema, and are utilized by implantation or insertion into a patient's eye. The present inventors analyzed the concentration of the therapeutic agent that would be found in selected eye tissue, namely the aqueous humour (AH) and the retina in order to determine the optimal location for such drug delivery systems to increase that concentration at the site of the tissue to be treated (the retina), while minimizing the concentration at other tissue (aqueous humour) so as to enhance efficacy and reduce undesirable side effects, such as IOP.

Figure 5:
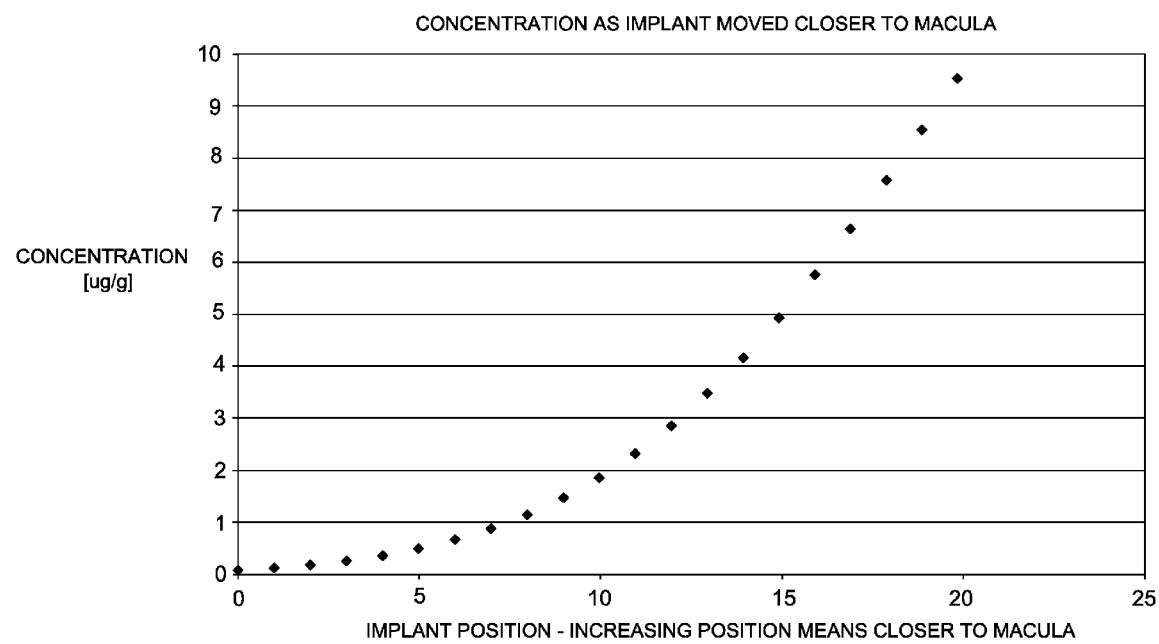
FIGS. 5-7 are graphical representation of the data presented in FIGS. 3-4.
Figure 6:
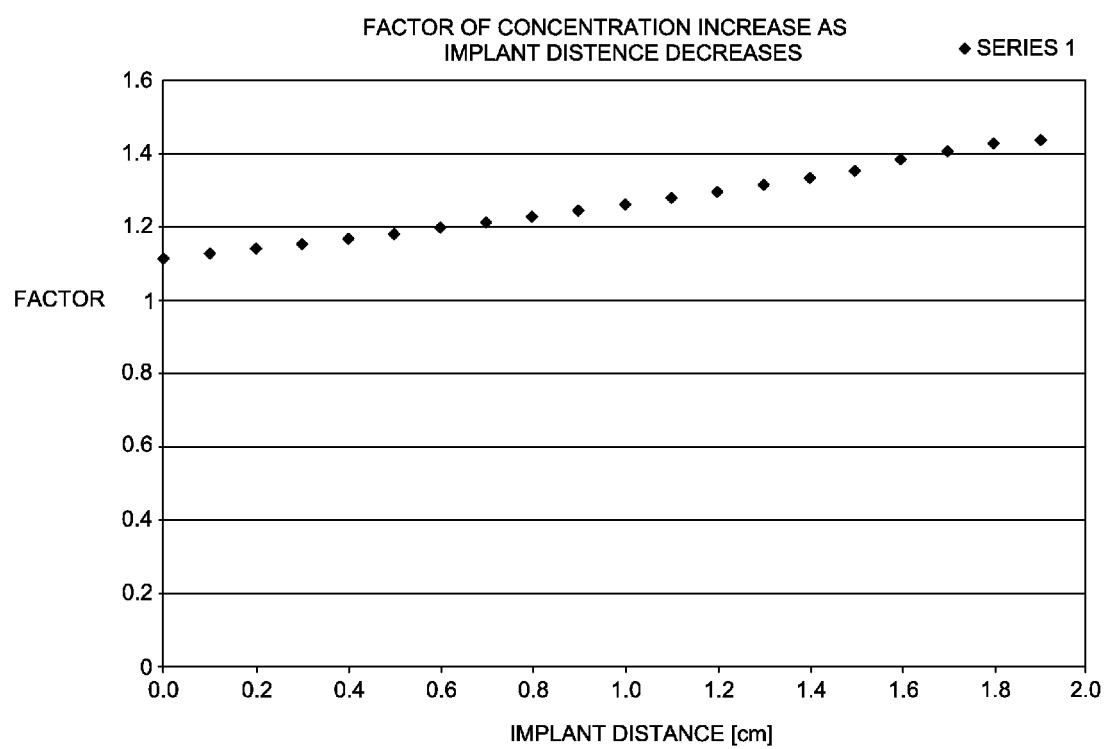
Figure 7:
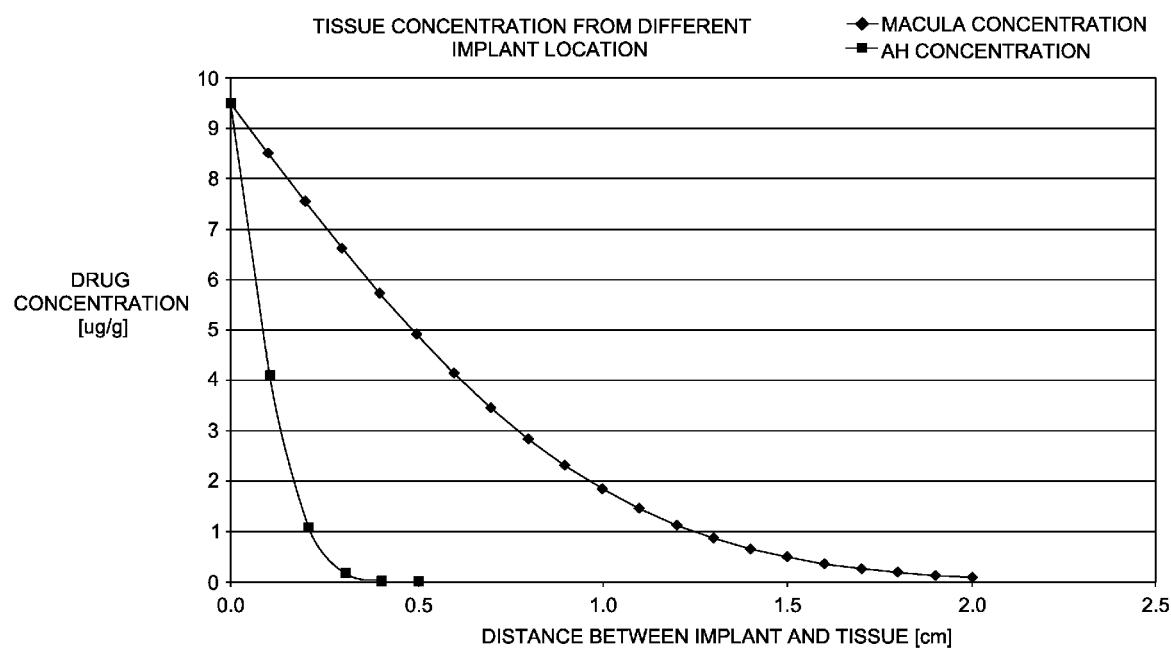

Those results are presented in tabular form in FIGS. 3 and 4, wherein the location of the implant from the tissue is noted in cm, specifically "x_AH [cm] D_AH" for the distance of the implant from the aqueous humour and "x_mac [cm] D_retina" for the distance of the implant from the macula. Concentration of the active ingredients is also presented for each implant expected at 13 days, 3 months and 6 months post implant. The results are also plotted with respect to the implant location and shown in FIGS. 5-7.

From these results, it is concluded that concentration of the desired active ingredient is increased in the desired tissue (e.g. the macula) as the implant in positioned closer to that tissue.

From a practical view point, the inventors have concluded that the known pars plana inserted corticosteroid eluting implants are the most inefficient method of delivering drug to the macula In fact, each millimeter that the implant is moved closer to the macula, creates a higher macular concentration (and lower anterior concentration which is good for avoiding IOP). In particular, at 13 days after implantation in the human eye, using a standard applicator, concentration of the therapeutic agent (e.g. dexamethasone) concentration of the agent can be 2.5 µg/g at the macula, and 0.0215 in the aqueous. Using a ½ inch needle, and placing the implant 4 mm deeper into the vitreous, macula concentration is increased 12 fold to 30.5 µg/g at the macula and aqueous levels are reduced to undetectable. As such, an implant located at the pars plana is not the ideal place for a corticosteroid implant, since it maximizes aqueous exposure and minimizes macular drug exposure. Accordingly, corticosteroid implants located posterior to the equator increase drug concentration to the macula 12 fold and decrease the aqueous humor concentrations to undetectable, as compared to placement anterior to the equator.

Figure 8:
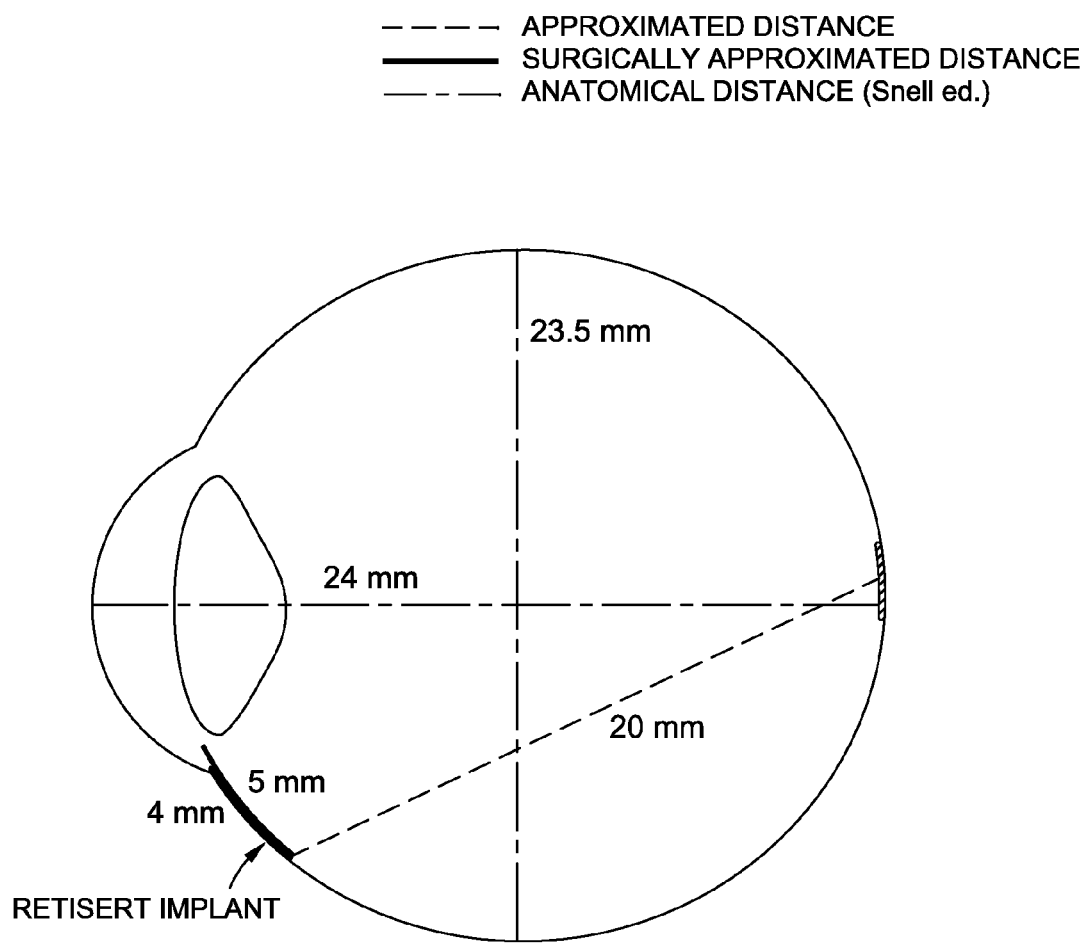
FIGS. 8-9 are representations of implant positions of current ocular implants.
Figure 9:
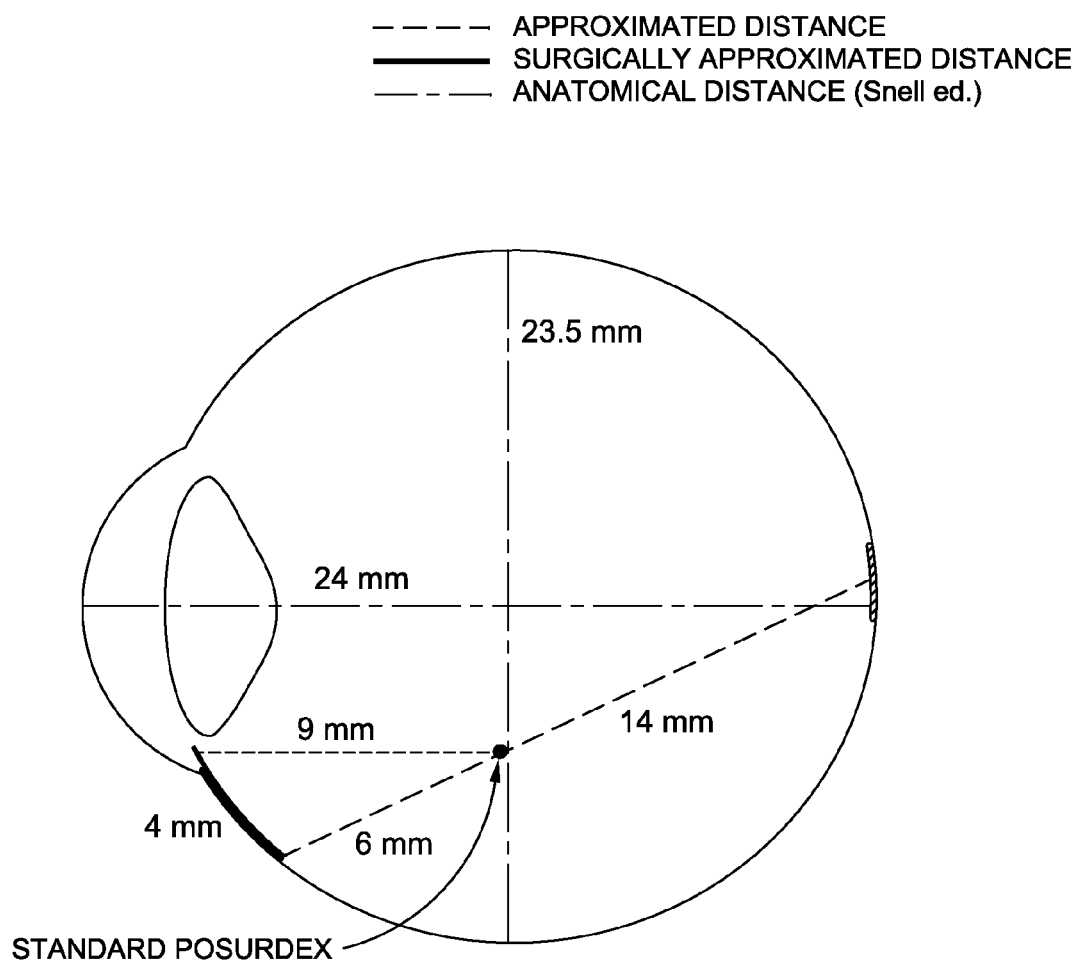
Figure 10:
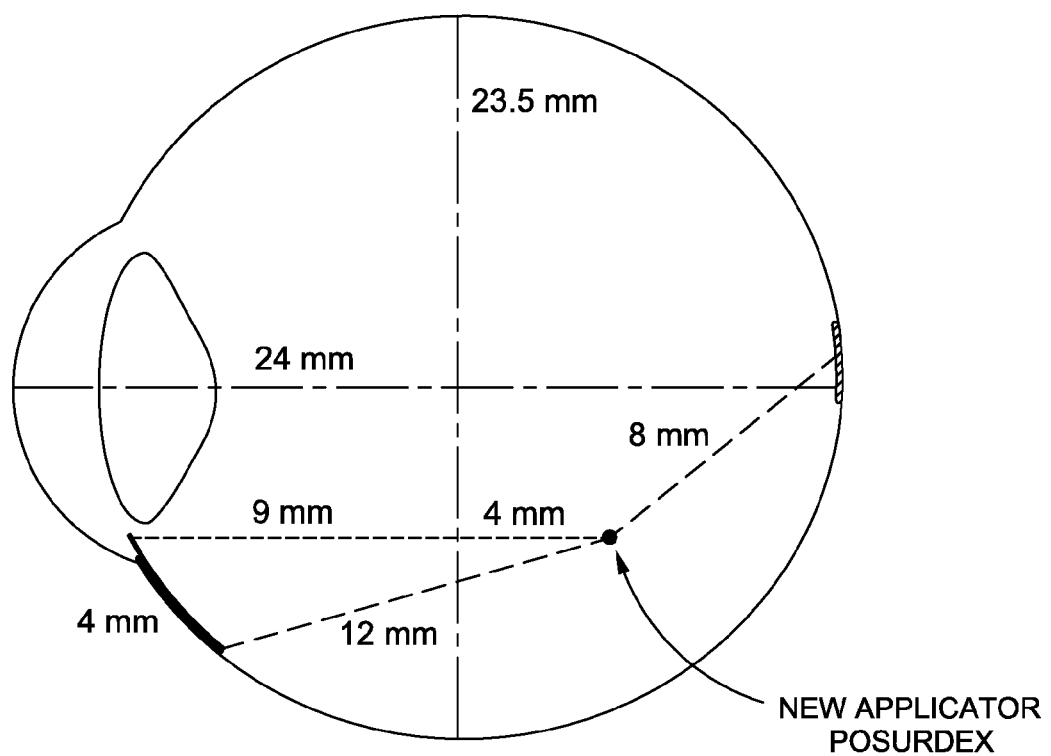
FIG. 10 shows an implant position according to the present invention.

The differences in implantation position can also be seen in FIGS. 8-10, wherein FIGS. 8 and 9 show the current standard implantation locations for two available products Retisert and Posurdex, respectively. FIG. 10 shows the more optimal position for a Posurdex implant according to the present invention wherein the implant is positioned closer to the macula to provide increase concentration of the active ingredient to the macula and nondetectable amounts of the active ingredient in the aqueous humour.

All references, articles, publications and patents and patent applications cited herein are incorporated by reference in their entireties.

We claim:

1. A method for treating macular edema with a biodegradable intraocular implant, the implant comprising a therapeutic agent and a biodegradable polymer associated with the therapeutic agent, wherein the implant is a cylindrical pellet with dimensions of about 2 mm×0.75 mm diameter, the method comprising the step of:
   placing the implant in the vitreous at a position x that is 1.3 cm from the aqueous humor and 0.8 cm from the macula thereby treating the macular edema.

2. The method of claim 1, wherein the placing step is carried out using an applicator with a ½ inch needle comprising a canula, in which canula the implant resides, wherein the needle has a length designed to permit placement of the drug delivery system into the vitreous at the position x.

3. The method according to any one of claim 1 or 2, wherein said therapeutic agent is a corticosteroid or an anti-VEGF antibody, wherein the corticosteroid is selected from the group consisting of fluocinolone, triamcinolone, and dexamethasone.

4. The method according to claim 3, wherein said therapeutic agent is at least one member selected from the group consisting of dexamethasone and fluocinolone, and said biodegradable polymer comprises at least one member selected from the group consisting of polylactides (PLA), polyglycolides (PGA), poly(lactide co-glycolide (PLGA), polycaprolactone, polyanhydride, poly methyl vinyl ether maleic anhydride, polycarbonates, polyarylates, polydioxanone, polyhydroxyalkanoates, and chitosan.

5. The method of claim 1, wherein the therapeutic agent is an anti-VEGF antibody.

* * * * *

UNITED STATES PATENT AND TRADEMARK OFFICE
CERTIFICATE OF CORRECTION

PATENT NO. : 8,571,802 B2
APPLICATION NO. : 11/948411
DATED : October 29, 2013
INVENTOR(S) : Michael R. Robinson et al.

It is certified that error appears in the above-identified patent and that said Letters Patent is hereby corrected as shown below:

On the title page, item (56), under "Other Publications", in column 2, line 3, delete "Opthalmology" and insert -- Ophthalmology --, therefor.

On the title page, item (56), under "Other Publications", in column 2, line 19, delete "1/070,158," and insert -- 11/070,158, --, therefor.

On the title page, item (56), under "Other Publications", in column 2, line 37, delete "transsleral" and insert -- transscleral --, therefor.

In the Drawings:

On sheet 1 of 10, line 5, delete "CILARY" and insert -- CILIARY --, therefor.

On sheet 1 of 10, line 7, delete "LIAGAMENT" and insert -- LIGAMENT --, therefor.

On sheet 1 of 10, line 11, delete "VITROUS" and insert -- VITREOUS --, therefor.

On sheet 6 of 10, line 2, delete "DISTENCE" and insert -- DISTANCE --, therefor.

In the Specifications:

In column 2, line 56, delete "Opthalmol" and insert -- Ophthalmol --, therefor.

In column 3, line 34, delete "cilliary" and insert -- ciliary --, therefor.

In column 3, line 39, delete "(10P)." and insert -- (IOP). --, therefor.

In column 3, line 44, delete "triamcinalone)" and insert -- triamcinolone) --, therefor.

In column 3, line 47, after "of" delete "a".

In column 3, line 51, after "of" delete "a".

In column 3, line 52, delete "intraviteal" and insert -- intravitreal --, therefor.

In column 5, line 63, delete "poly (lactide-co-glycolides)," and insert -- poly(lactide-co-glycolide), --, therefor.

Signed and Sealed this
Twenty-fifth Day of February, 2014

Michelle K. Lee
*Deputy Director of the United States Patent and Trademark Office*

In column 5, lines 66-67, delete "poly(lactide co-glycolide" and insert -- poly(lactide-co-glycolide) --, therefor.

In column 6, line 16, delete "canula" and insert -- cannula --, therefor.

In column 6, line 32, delete "corticosteriod," and insert -- corticosteroid, --, therefor.

In column 10, line 62, delete "implant" and insert -- implant. --, therefor.

In column 12, line 15, delete "serpignous" and insert -- serpiginous --, therefor.

In column 12, line 22, delete "telangiectasis," and insert -- telangiectasia, --, therefor.

In column 12, line 24, delete "angitis," and insert -- angiitis, --, therefor.

In column 14, line 33, delete "fluoroquinilones," and insert -- fluoroquinolones, --, therefor.

In column 14, line 56, delete "Opthalmology" and insert -- Ophthalmology --, therefor.

In column 14, line 60, delete "compounds" and insert -- compounds. --, therefor.

In column 15, line 27, delete "log P," and insert -- logP, --, therefor.

In the Claims:

In column 16, line 60, in claim 2, delete "canula," and insert -- cannula, --, therefor.

In column 16, line 60, in claim 2, delete "canula" and insert -- cannula --, therefor.

In column 17, line 6, in claim 4, delete "poly(lactide co-glycolide" and insert -- poly(lactide-co-glycolide) --, therefor.